US008961489B2

(12) United States Patent
Schwarz et al.

(10) Patent No.: US 8,961,489 B2

(45) Date of Patent: Feb. 24, 2015

(54) BLOOD PLASMA STORAGE BOTTLE WITH LOCKING CAP

(75) Inventors: Donald Schwarz, Bridgewater, MA (US); Seth Kasper, Cambridge, MA (US); Ron Marek, Kingswood, TX (US); Graeme Struthers, Scotland (GB)

(73) Assignee: Haemonetics Corporation, Braintree, MA (US)

( * ) Notice: Subject to any disclaimer, the term of this patent is extended or adjusted under 35 U.S.C. 154(b) by 284 days.

(21) Appl. No.: 13/696,956

(22) PCT Filed: May 12, 2010

(86) PCT No.: PCT/US2010/034569

§ 371 (c)(1), (2), (4) Date: Jan. 23, 2013

(87) PCT Pub. No.: WO2011/142752

PCT Pub. Date: Nov. 17, 2011

(65) Prior Publication Data

US 2013/0123725 A1 May 16, 2013

(51) Int. Cl.

*A61B 19/00* (2006.01)

*B65D 41/04* (2006.01)

(Continued)

(52) U.S. Cl.

CPC *A61J 1/1412* (2013.01); *A61J 1/14* (2013.01); *B65D 47/2043* (2013.01); *A61J 1/1437* (2013.01)

USPC ............ 604/403; 215/329; 215/330; 215/331

(58) Field of Classification Search

CPC ... A61J 1/05; A61J 1/1412; A61J 2001/1418; A61J 2001/1425

USPC .......... 604/403–416, 327–329; 215/208, 235, 215/247–249, 329–340

See application file for complete search history.

(56) References Cited

U.S. PATENT DOCUMENTS 3,952,902 A 4/1976 Prouty et al. .................. 215/306

4,568,345 A 2/1986 Keilman et al. ............... 604/403

(Continued)

FOREIGN PATENT DOCUMENTS

CN 2199152 Y 5/1995 ............ B65D 81/32

CN 2665055 Y 12/2004 ............ B65D 83/32

(Continued)

OTHER PUBLICATIONS

Notification of Reason for Rejection—Patent Application No. 2013-510,059, 2 pages, Dated Mar. 18, 2014.

(Continued)

*Primary Examiner* — Philip R Wiest

*Assistant Examiner* — Benjamin Klein

(74) *Attorney, Agent, or Firm* — Sunstein Kann Murphy & Timbers LLP

(57) ABSTRACT

A container for storing donated blood plasma has a neck and an attachable locking cap. The cap may be rotatably attached to the neck. The cap and the neck are configured to lock the cap in at least one, and preferably two, rotational positions. In one position, tubes connected to the container are accessible. After the plasma has been collected and the tubes have been cut off and sealed, in the other position, the tube stubs are protected by the cap. The bottle and the cap may define structures that facilitate storing and protecting tubing wrapped longitudinally around the container, until the container is used to collect and store plasma.

24 Claims, 8 Drawing Sheets

(51) Int. Cl.
*A61J 1/14* (2006.01)
*B65D 47/20* (2006.01)

(56) References Cited

U.S. PATENT DOCUMENTS

| | | | | |
|---|---|---|---|---|
| 5,132,026 | A | 7/1992 | Baluyot et al. | 210/767 |
| 2011/0284413 | A1 | 11/2011 | Meise | 206/438 |

FOREIGN PATENT DOCUMENTS

| | | | | |
|---|---|---|---|---|
| CN | 1878703 | A | 12/2006 | B65D 55/02 |
| DE | 43 17 316 | A1 | 12/1994 | A61M 31/00 |
| DE | 20 2009 001 068 | U1 | 5/2009 | A61J 1/05 |
| DE | 20010825 | U1 | 10/2010 | A61J 1/05 |
| JP | 53-19276 | | 2/1978 | B65D 1/00 |
| JP | 3-11648 | | 2/1991 | B65D 41/04 |
| JP | 5-77039 | | 10/1993 | B65D 43/02 |
| JP | 2008-237781 | A | 10/2008 | A61B 5/15 |
| JP | 2009-125162 | A | 6/2009 | A61J 1/16 |
| WO | WO 2005/004783 | | 1/2005 | A61J 1/00 |
| WO | WO 2005/037659 | | 4/2005 | |

OTHER PUBLICATIONS (English translation), Notification of Reason for Rejection—Patent Application No. 2013-510,059, 2 pages, Dated Mar. 18, 2014.

State Intellectual Property Office of the People's Republic of China, Notification of First Office Action—Application No. 201080067584.4, 15 pages, Date of Notification: May 6, 2014.

State Intellectual Property Office of the People's Republic of China (English translation), Notification of First Office Action—Application No. 201080067584.4, 12 pages, Date of Notification: May 6, 2014.

Fenwal, Inc., 5.510(K) Summary-Plasma Pooling Bottles, 4 pages, May 16, 2008.

Fenwal, Plasmacell-C Product Performance Report, Jan. 2010.

International Searching Authority, International Application No. PCT/US2010/034569, dated Mar. 3, 2011, together with the Written Opinion of the International Searching Authority, 10 pages.

European Patent Office, Communication Pursuant to Rules 161(1) and 192 EPC from the European Patent Office pertaining to International Application No. 10723853.7-1257, 2 pages, Dec. 12, 2012.

BLOOD PLASMA STORAGE BOTTLE WITH LOCKING CAP

CROSS REFERENCE

This application is a §371 application of International Patent Application PCT/US2010/034569 filed May 12, 2010, the contents of which are incorporated herein by reference.

TECHNICAL FIELD

The present invention relates to blood plasma storage containers and, more particularly, to such containers having locking caps.

BACKGROUND ART

Blood plasma is a straw-colored liquid component of whole blood, in which blood cells, such as red blood cells and white blood cells, and other components of the whole blood are normally suspended. Whole blood is made up of about 55%, by volume, plasma. Plasma plays important roles in a body's circulatory system, including transporting blood cells, conducting heat and carrying waste products. Pure plasma contains clotting factors, which increase the rate at which blood clots, making it useful in surgery and in the treatment of hemophilia. Banked whole blood is sometimes used to replace blood lost by patients during surgery or as a result of traumatic injuries. However, if banked whole blood of a type compatible with a patient is not available, plasma may sometimes be used to replace some of the lost blood. Furthermore, plasma may be frozen and stored for relatively long periods of time until it is needed.

Plasma is collected from donors. Sometimes, whole blood is collected from a donor, and plasma is separated from the other components of the donated whole blood later, such as in a laboratory. However, in other cases, the plasma is separated from the other components of the whole blood at the donation site, and the other components are returned to the circulation system of the donor. Apheresis is a medical technology in which the blood of a donor or patient is passed through an apparatus, such as a centrifuge, that separates out one particular constituent and returns the remainder to the donor or patient. Plasmapheresis is a medical therapy that involves separating blood plasma from whole blood.

Donated whole blood is typically stored in plastic bags. However, collected donated plasma is typically stored in plastic bottles. A typical plasma bottle includes a closed neck with at least one nipple for connecting plastic tubing. Often, two nipples are provided, one for introducing plasma into the bottle, and the other for venting air out of the bottle. After plasma has been collected in the bottle, the tubing is cut off using heat-sealing tongs, leaving short (typically about 1½ inch long) sealed tubing stubs attached to the nipples.

These stubs typically project from the bottle neck and may pose problems during transport and storage. For example, when the plasma is frozen, the plastic of the stubs becomes brittle and may break, thereby violating the requirement to keep the plasma in an aseptic container. Prior art plasma bottles have been designed to attempt to overcome problems associated with the stubs.

For example, German Utility Model DE 200 10 825 U 1, the entire contents of which are hereby incorporated by reference, discloses a plasma bottle with a rotatable protective cap with at least one slot. Two sealed tube stubs project through respective slots, until the cap is rotated. Rotating the cap draws the stubs inside the cap, where they are physically protected from impact. The cap includes a resilient rib and tabs on the inside cylindrical surface of the cap. The rib and tabs project radially inward. The bottle neck includes fins that project radially outward. The fins and the rib and tabs cooperate to create a stop to inhibit rotation of the cap from one of two positions. However, this design does not fully solve the problems associated with plasma collection bottles. For example, the stop is easily overcome. Furthermore, the cap may be relatively easily dislodged from the bottle, such as when several bottles are packaged together in a container for shipment or storage.

SUMMARY OF EMBODIMENTS

An embodiment of the present invention provides a container for collecting and storing blood plasma. The container includes a bottle and a cap. The bottle includes a neck, which includes a disc-shaped neck track. The track including a first key. For example, the key may be a rectangular member (as viewed in the plane of the neck track) that extends radially outward from the edge of the track. The container includes means for permitting fluid communication into and out of an interior of the bottle. A flexible tube may be attached at one end to the means for permitting fluid communication, and the flexible tube may be sealed at its other end. In some embodiments, the container includes two or more ports, each of which is in fluid communication with an interior of the bottle. Each port may include a nipple, to which a flexible tube may be connected. The other end of the tube may be sealed.

The cap is attachable to the neck of the bottle. (A cap that is already attached to the bottle is, nonetheless, referred to herein as being "attachable" to the bottle.) The cap has an internal cap track sized and positioned to cooperate with the neck track. The cap is configured to permit the cap to rotate about the neck track. The cap defines a slot. The slot is sized and positioned to interlock with the first key at a first (open) rotational position of the cap. When the cap is in this open position, the means for permitting fluid communication or the ports are accessible from outside the cap. For example, the tubes may extend through the slot.

The cap may also define a second key sized and positioned to interlock with the first key at a second (closed) rotational position of the cap. For example, the cap may define a pocket shaped to accept the key extending radially outward from the neck track. When the cap is rotated to the closed position, the means for permitting fluid communication or the ports are inaccessible, via the slot, from outside the cap.

To facilitate wrapping the tubes longitudinally around the container, the bottle has a bottom and a major longitudinal axis and defines a recess across a diameter of the bottom of the bottle. The cap may include two spaced-apart vanes extending in directions substantially parallel to the major longitudinal axis of the bottle. At the first rotational position of the cap, the vanes are substantially parallel to the recess in the bottom of the bottle.

At the first (open) rotational position of the cap, the means for permitting fluid communication or the ports are accessible from outside the cap via the slot. At the second (closed) rotational position of the cap, the means for permitting fluid communication or the ports are inaccessible from outside the cap via the slot.

A flexible tube may be attached at one end to the means for permitting fluid communication or to one of the ports, and the tube may be sealed at the other end. Similarly, a second flexible tube may be attached to the other port. The interior of the bottle may be sterile.

The key on the neck track may be radially proud of the neck track. As noted, the key on the neck track may be rectangular and extend radially away from the neck track. Thus, three edges of the key may be distinct from the circular shape of the neck track. These three edges may lie in a plane of the neck track. The second edge may be parallel to a line tangent to the neck track.

The cap may define the second key as a recess shaped to accept the first key.

The cap may include one or more radially inwardly projecting tabs on an inside wall of the cap. Each tab may define at least part of the internal cap track. Each tab may be located proximate a circumferential edge of the cap. In addition, the cap may include at least one radially inwardly projecting track element on an inside wall of the cap. Each track element may be spaced from the circumferential edge of the cap a distance selected to accommodate the disc-shaped neck track between the tab(s) and the track element(s). Each tab may be sized and configured to at least partially prevent a top of another cap from nesting within the cap. The cap shape may be configured to at least partially prevent nesting of the cap within another cap.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Embodiments of the present invention include containers having locking caps for storing blood plasma and protecting tube stubs during storage and transportation. One such container includes a bottle having a neck and a cap rotatably attached to the neck. The bottle and the cap may define structures that facilitate storing and protecting tubing wrapped longitudinally around the container, until the container is used to collect and store plasma. The cap and the neck are configured to lock the cap in at least one, and preferably two, rotational positions. In one position, the tubes connected to the container are accessible. After the plasma has been collected and the tubes have been cut off and sealed, in the other position, the tube stubs are protected by the cap.

Figure 1:
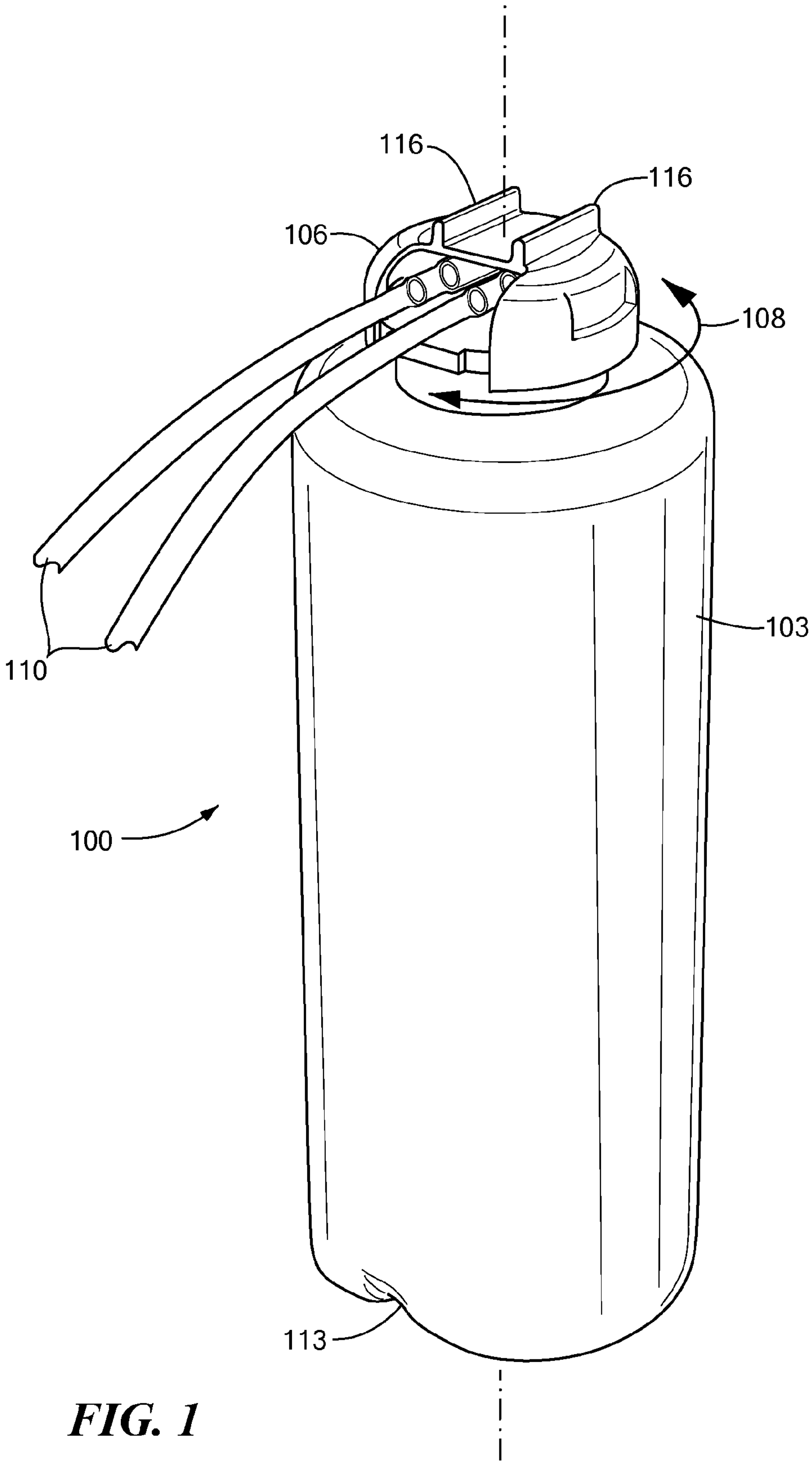
FIG. 1 is perspective view of a blood plasma container with a locking cap, according to an embodiment of the present invention.

FIG. 1 is a perspective view of a blood plasma container 100, according to an embodiment of the present invention. The container 100 includes a bottle 103 and a cap 106 rotatably attached to the bottle 103. The bottle 103 and the cap 106 may be made of any suitable material or materials. The cap 106 locks in at least one, and preferably two, rotational positions approximately 180 degrees apart. In use, the container 100 is connected via one or more flexible tubes 110 to blood collection and apheresis equipment (not shown). For clarity, only portions of the tubes 110 are shown in FIG. 1. Once collected plasma has been introduced into the container 100 and the tubes 110 have been cut off and sealed, and the sealed tube stubs have been tucked under the cap 106 (as described in more detail below), the cap 106 may be rotated, as indicated by an arrow 108, approximately 180 degrees in either direction to protect the tube stubs.

Figure 2:
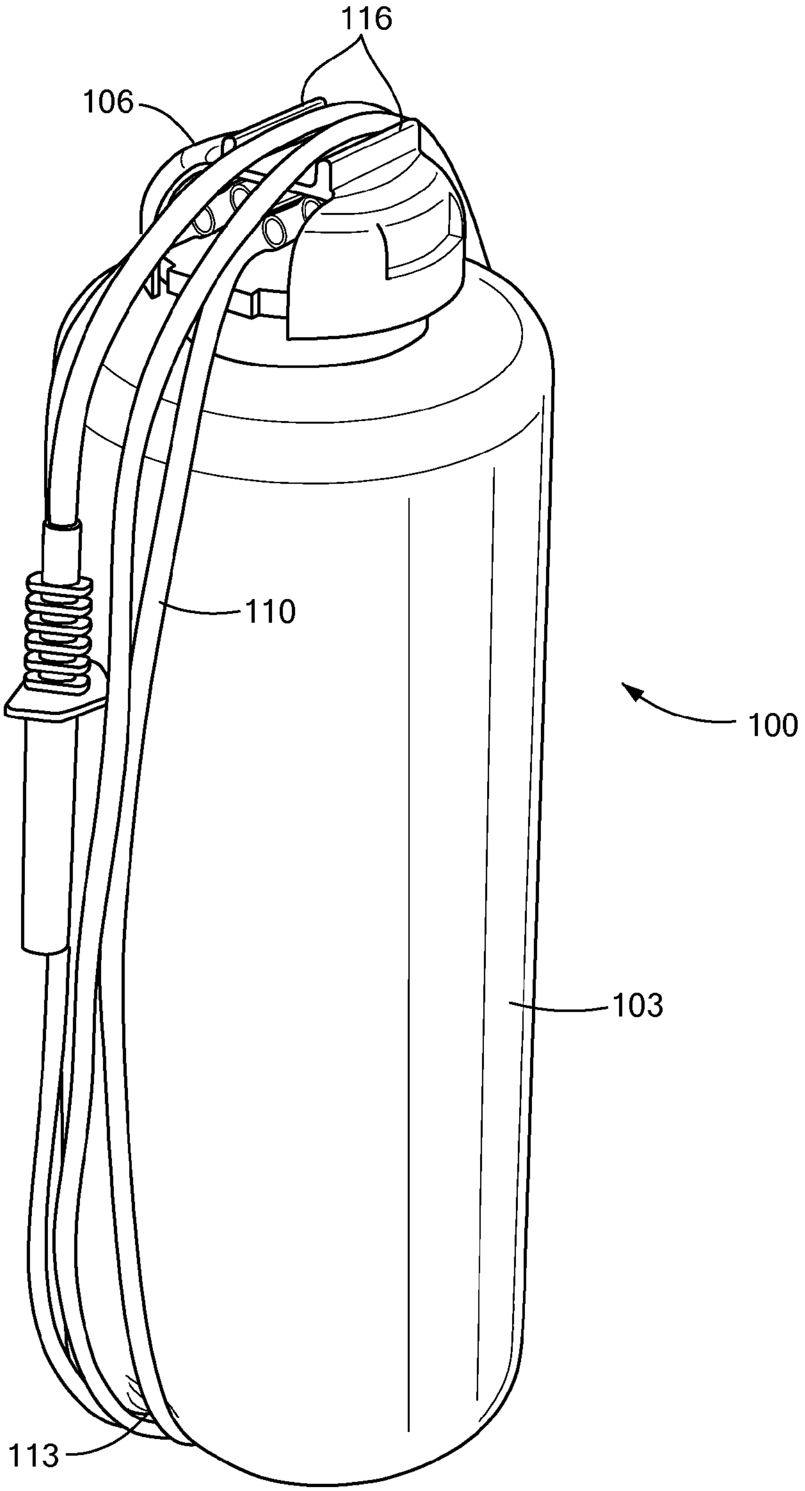
FIG. 2 is perspective view of the container of FIG. 1 with tubes wrapped longitudinally around the container, according to an embodiment of the present invention.

During manufacture, the tubes 110 may be connected to the container 100. To facilitate storage and transportation of the container 100 before it is used, the tubes 110 may be wrapped longitudinally around the container 100, as shown in FIG. 2. Returning to FIG. 1, the bottle 103 defines a recess 113 in the bottom of the bottle 103. This recess is shown more clearly in FIG. 3, which is provides close-up perspective view of the bottom 300 of the bottle 103. The recess 113 may extend across a diameter of the bottom of the bottle 103. The recess 113 should be deep enough to accommodate at least one layer of the tubes 110. The recess 113 should be wide enough to accommodate as many turns of the tubes 110 as necessary or desired, based on the length of the tubes 110.

Returning to FIG. 1, the top of the cap 106 includes two vanes 116 extending in a direction parallel to a major longitudinal axis 120 of the bottle 103. The vanes 116 prevent the tubes 110 wrapped around the container 100 from sliding off the cap 106. The vanes 116 should be tall enough to accommodate at least one layer of the tubes 110. The vanes 116 should be spaced apart far enough to accommodate as many turns of the tubes 110 as necessary or desired, based on the length of the tubes 110.

Thus, collectively, the vanes 116 and the recess 113 provide guides, within which the tubes 110 may be wrapped. Wrapping the tubes 110 around the container 100 and within the vanes 116 and the recess 113 prevents the tubes 110 from kinking or becoming entangled with tubes connected to other containers during shipment and storage. In addition, the vanes 116 and the recess 113 protect the tubes 110 from damage during shipment and storage, when similar containers may be stacked on top of one another. In this regard, the vanes 116 may be configured to be tall enough, and the recess 113 may be configured to be deep enough, to protect the tubes 110 from being contacted or crushed by other containers.

Figure 3:
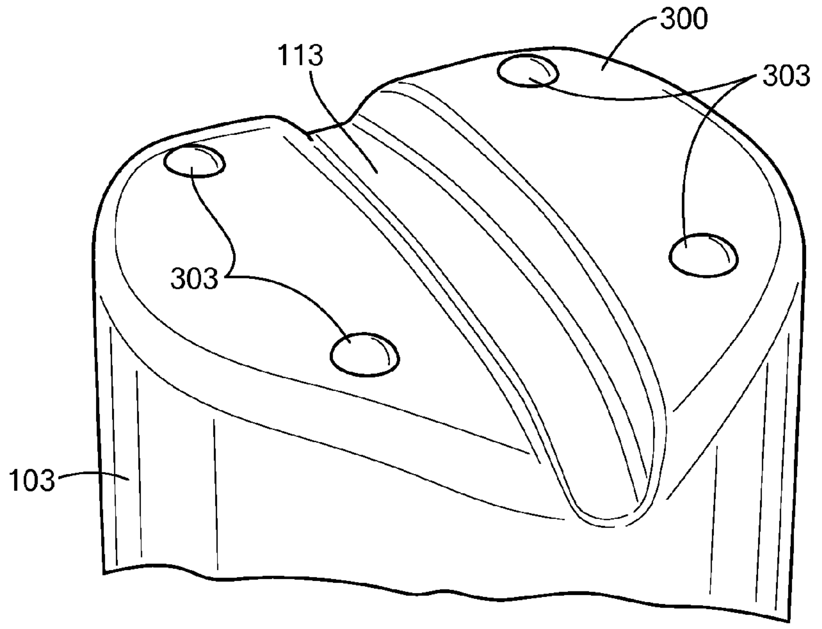
FIG. 3 is a perspective view of the bottom of the container of FIG. 1.

As shown in FIG. 3, the bottom of the bottle 103 may include one or more raised feet 303, on which the container may stand, such as when used on a horizontal surface, or to provide additional separation between adjacent stacked containers during shipment or storage. Optionally, the vanes 116 or the recess 113 may be used by automated manufacturing equipment to grip or orient the cap 106 or the bottle 103 as needed, such as when the cap 106 is attached to the bottle 103.

Figure 4:
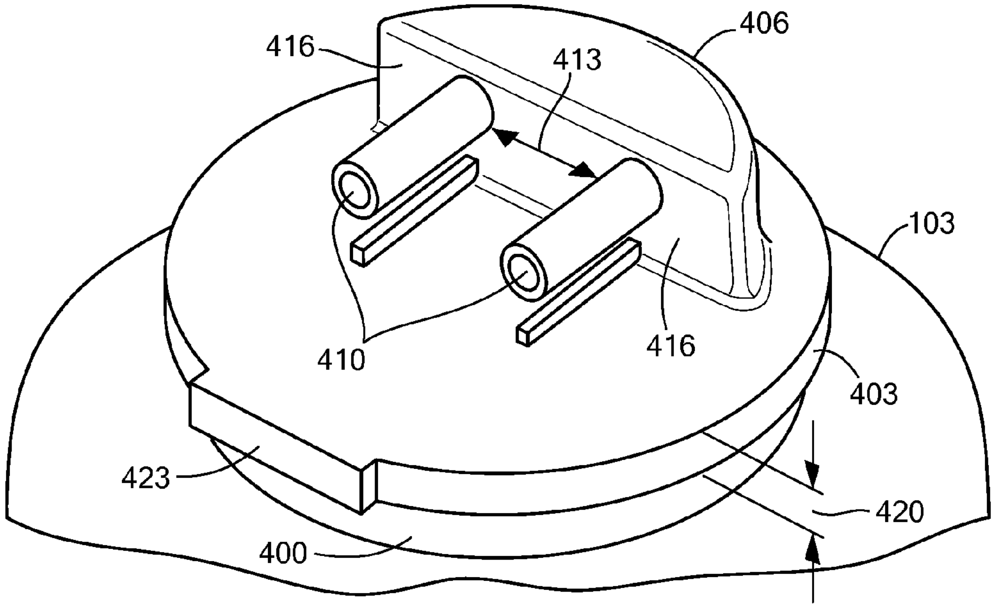
FIG. 4 is a perspective view of a neck portion of the container of FIG. 1, with the cap removed.
Figure 5:
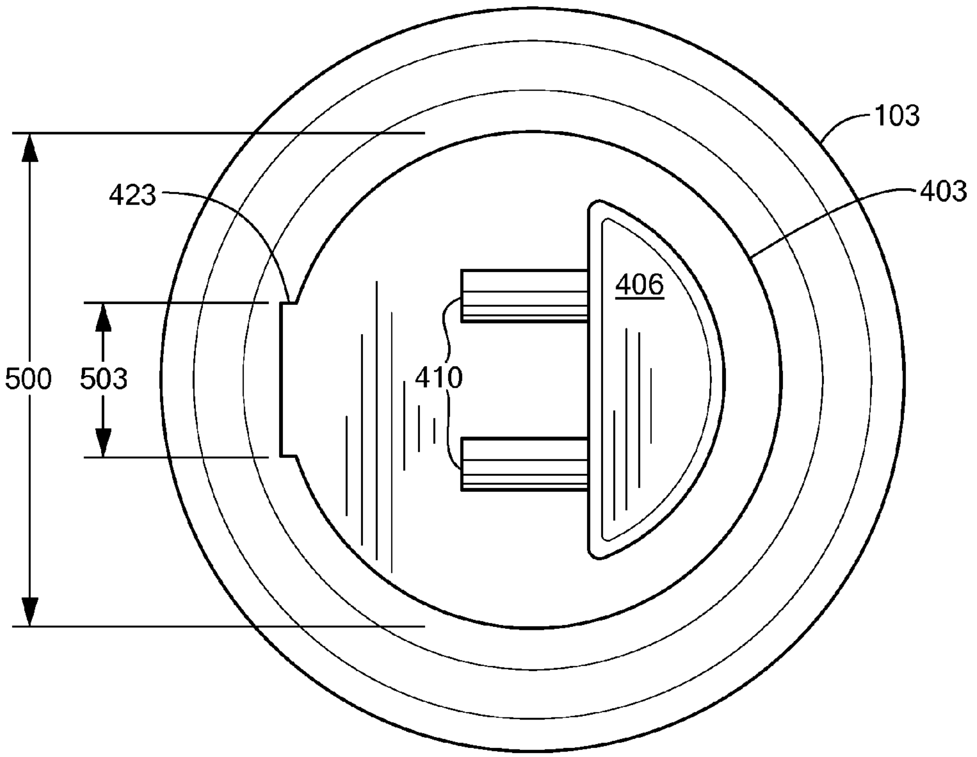
FIG. 5 is a top view of the neck portion of the container of FIG. 1, with the cap removed.
Figure 6:
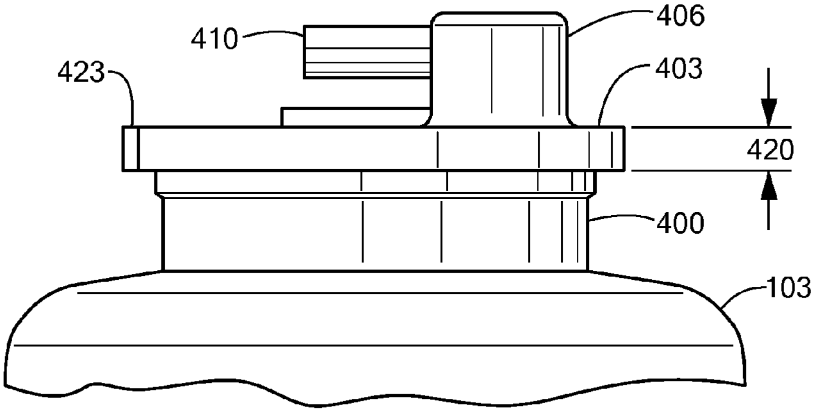
FIG. 6 is a side view of the neck portion of the container of FIG. 1, with the cap removed.

FIG. 4 is a close-up perspective view of a neck portion of the bottle 103, with the cap 106 removed for clarity. FIG. 5 is a top view, and FIG. 6 is a side view, of the neck portion of the bottle 103, with the cap removed for clarity. A hollow neck 400 connects a disc-shaped platform 403 to the rest of the bottle 103. A hollow raised curved structure 406 is connected to the platform 403. One or more nipples 410 are connected to the hollow raised structure 406 (best seen in FIG. 4). The nipples 410 are in fluid communication with the interior of the bottle 103. Otherwise, the bottle 103 is closed to the outside. The nipples 410 may be spaced apart a distance 413 to accommodate tucking in two tube stubs, as described below. Optionally or alternatively, space 416 may be provided radially outwardly from the nipples 410 to accommodate the tube stubs.

One end of each of the tubes 110 (FIGS. 1 and 2) may be connected to each of the nipples 410. The other end of the tube may be connected to, or is capable of being connected to, the rest of the plasma-collection system, or the end may be heat sealed (not shown). Preferably, the interior of the bottle 103 is sterile, and this sterility is maintained by the closed or sealed ends of the tubes 110.

Figure 7:
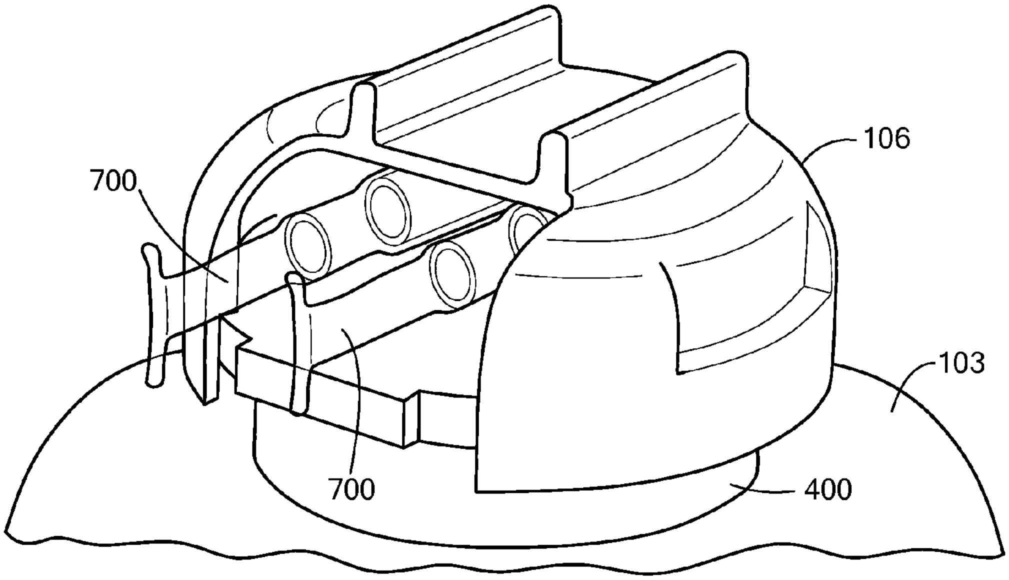
FIG. 7 is a perspective view of the neck portion of the container of FIG. 1, with the cap installed in a first (open) position with sealed-off tubes extending through an opening in the cap.

After plasma has been collected and stored in the container 100, the tubes 110 may be cut off and heat sealed, as is well known in the art. The neck portion of the container 100, after the tubes 110 have been cut off and sealed, is shown in FIG. 7. The cutting and sealing process leaves short tube stubs 700 connected to the nipples 410. The tubes 110 should be cut so as to leave relatively short, such as about 1½ inch long, stubs 700.

Figure 8:
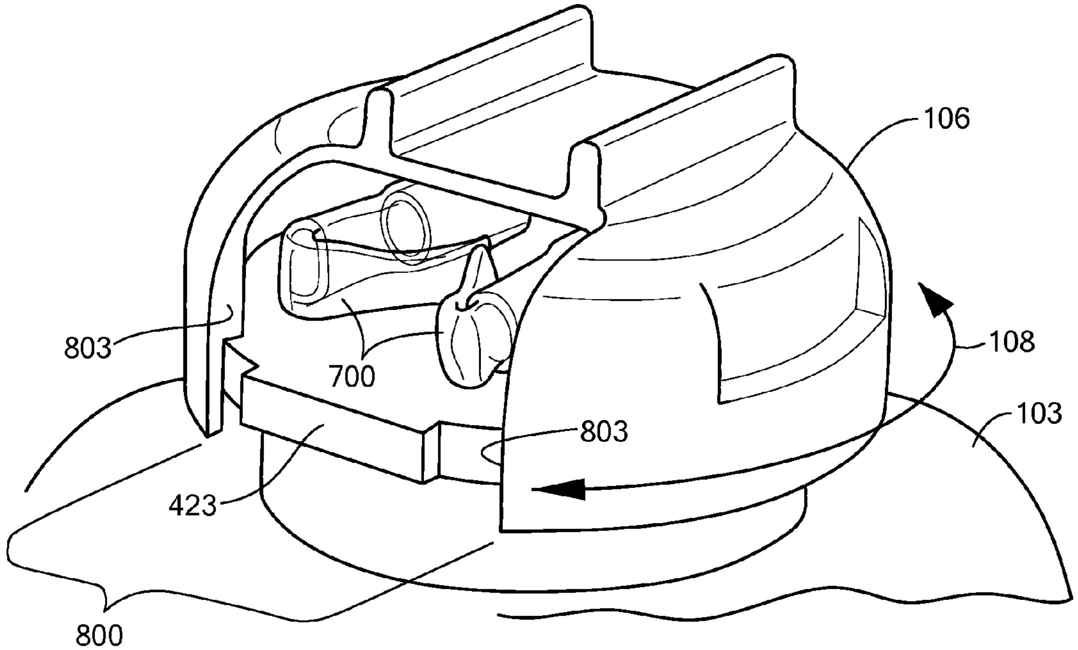
FIG. 8 is a perspective view of the neck portion of the container of FIG. 1, with the cap installed in the first (open) position with the sealed-off tubes tucked into in the cap.

In preparation for closing the cap 106, the stubs 700 should be folded inward toward each other, and the ends of the stubs 700 should be tucked in to the space between the nipples 410, as shown in FIG. 8. Optionally or alternatively, one or both of the stubs 700 may be tucked in to the spaces 416 (FIG. 4) on the other sides of the nipples 410.

Figure 9:
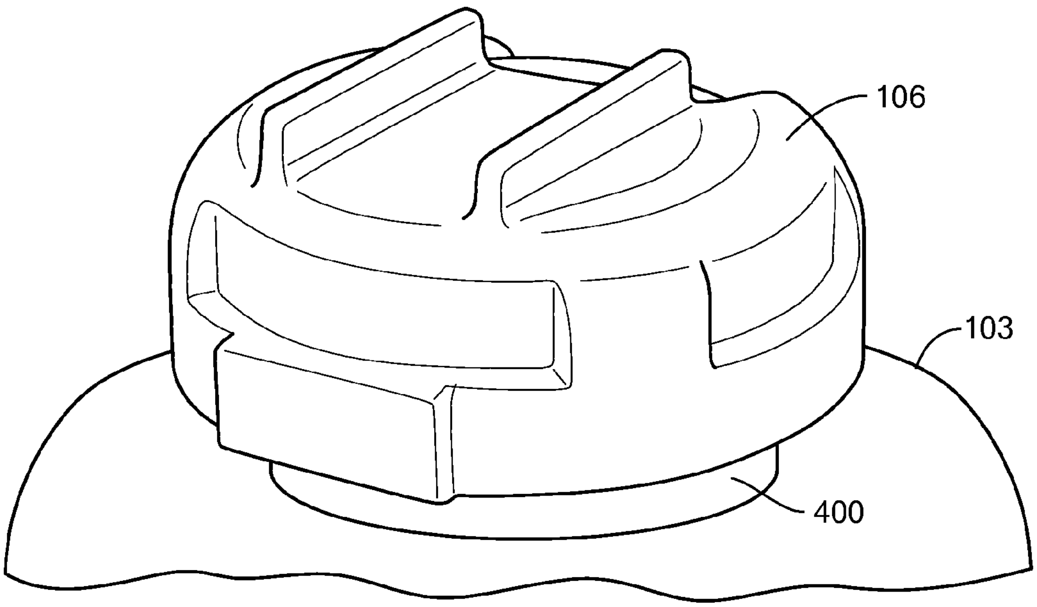
FIG. 9 is a perspective view of the neck portion of the container of FIG. 1, with the cap installed in a second (closed) position.

In either case, once the stubs 700 are tucked in, the cap 106 may be rotated approximately 180 degrees in either direction, as indicated by the arrow 108. As shown in FIG. 9, after the cap 106 has been rotated, the stubs 700 are covered and protected by the cap 106.

As noted, the cap 106 locks in one, or preferably two, rotational positions. In a first position (shown in FIG. 8), the tubes 110 or the stubs 700 are accessible from outside the cap 106, whereas in a second position (shown in FIG. 9), the stubs 700 are inaccessible from outside the cap 106. The disc-shaped platform 403 (FIG. 4) and structures in the cap 106 facilitate the rotation and the locking of the cap 106, as described below.

Figure 10:
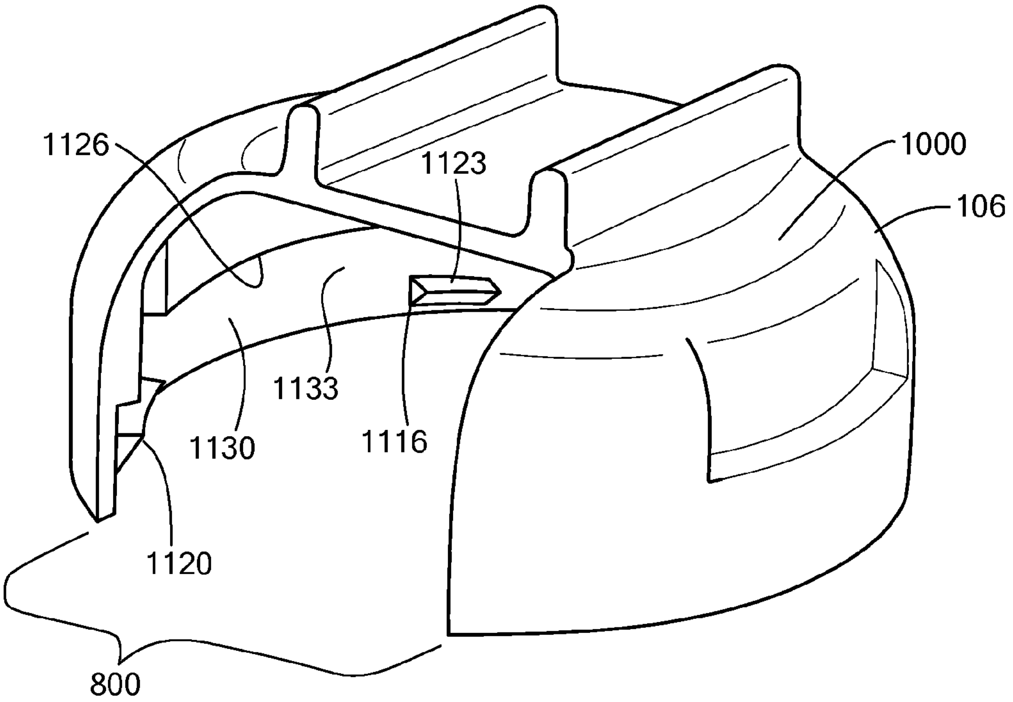
FIGS. 10 and 11 are perspective views from above and from below, respectively, of the cap of the container of FIG. 1.
Figure 11:
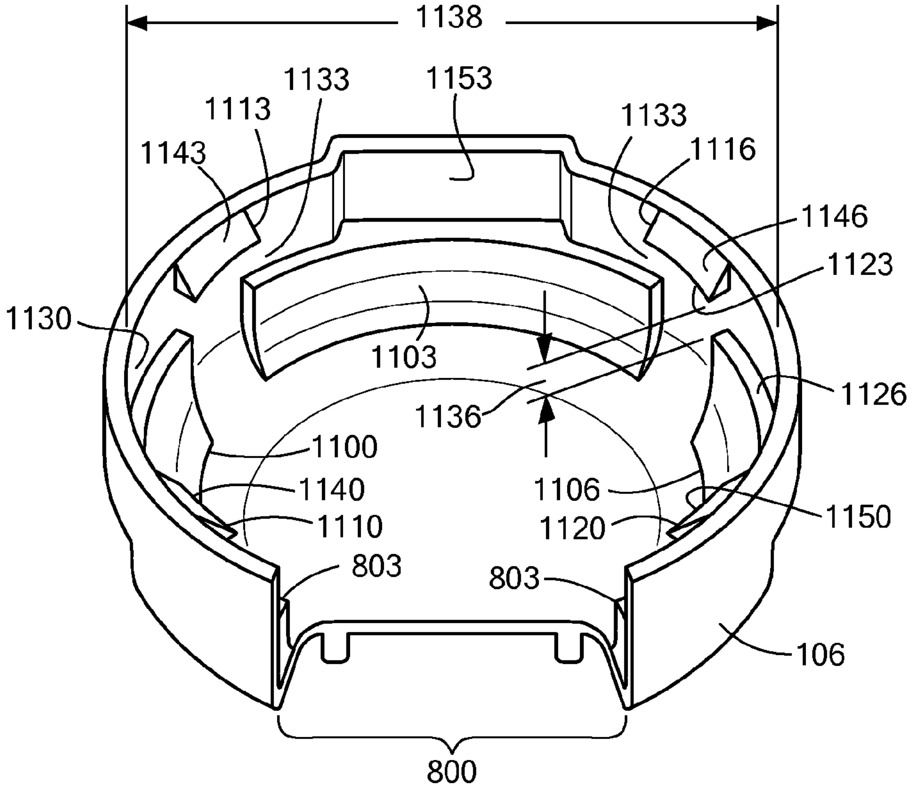

FIGS. 10 and 11 are perspective views of the cap 106 from above and below, respectively. The cap 106 includes inwardly projecting track elements 1100, 1103 and 1106, as well as angled inwardly projecting retaining tabs 1110, 1113, 1116 and 1120. The track elements 1100-1106 and the tabs 1110-1120 provide surfaces, exemplified by surfaces 1123 and 1126, that face in opposite directions. The cylindrical inside wall 1130 of the cap 106, together with the track elements 1100-1106 and the tabs 1110-1120, collectively define an annular track 1133 bounded on the outside by the inside wall 1130, and bounded above and below by the surfaces 1123 and 1126.

Figure 12:
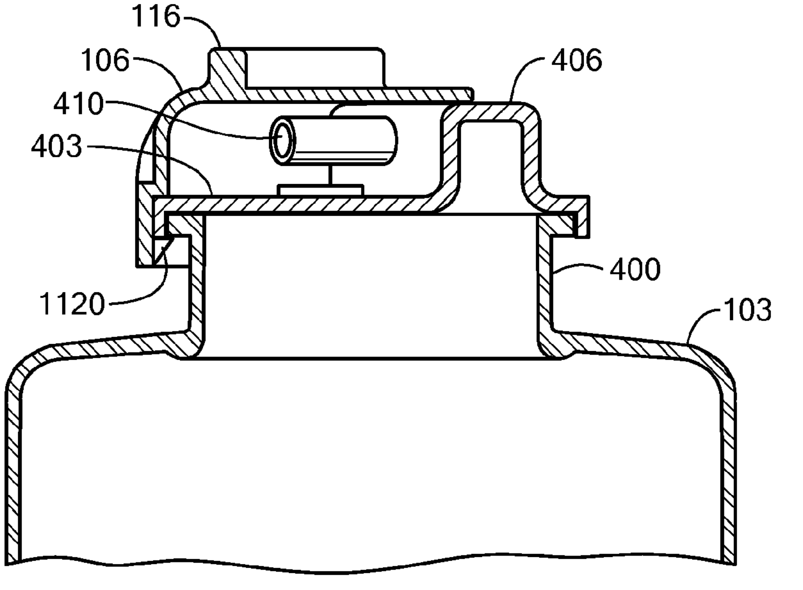
FIG. 12 is a cross-sectional view of the neck portion of the container of FIG. 13.

The annular track 1133 is sized and configured to accommodate and capture the disc-shaped platform 403 within the track 1133. In other words, the distance 1136 between the opposite-facing surfaces 1123 and 1126 is approximately equal to the thickness 420 (FIGS. 4 and 6) of the platform 403, and the inside diameter 1138 of the cap 106 is approximately equal to the diameter 500 (FIG. 5) of the disc-shaped platform 403. Thus, when the platform 403 is disposed within the track 1133, the cap 106 may be rotated about the major longitudinal axis 120 of the bottle 103. Angled surfaces 1140, 1143, 1146 and 1150 on the tabs 1110-1120 facilitate attaching the cap 106 to the platform 403, such as by pressing the cap 106 down onto the platform 403. As the cap 106 is pressed onto the platform 403, the angled surfaces 1140-1150 cause the walls of the cap 106 to deform slightly radially outward as the tabs 1110-1120 step over the platform 403. Once the cap 106 is in place, walls of the cap 106 rebound, and the platform 403 remains captured between the track elements 1100-1106 and the tabs 1110-1120, as shown in cross-section in FIG. 12.

As noted, the disc-shaped platform 403 is captured within the track 1133. "Captured" here means the cap 106 may be rotated about the disc-shaped platform 403; however, more force than would normally be applied during use of the container 100 is required to remove the cap 106 from the platform 403, and continued rotation of the cap 106 does not unscrew the cap 106 from the bottle 103. Thus, the cap 106 remains attached to the bottle 103 more robustly than in the prior art. As noted, the cap 106 is attached to the bottle 103, meaning the cap 106 is captured.

A shoulder portion 1000 (FIG. 10) of the cap 106 and the radially inwardly oriented tabs 1110-1120 (FIG. 11) prevent the top of another cap from entering and becoming lodged within the cap 106 (referred to as the other cap "nesting" within the cap 106), as may otherwise occur after the caps are manufactured and many such caps are stored or shipped together in a container or during an automated process for assembling caps and bottles. The shoulder portion 1000 is broad enough to prevent much or any of the shoulder portion 1000 from passing the tabs 1110-1120. In addition, the inside diameter of the track elements 1100-1106 may be too small to admit much or any of the shoulder portion 1000 of a cap. In general, the cap 106 may be shaped to prevent or minimize nesting.

To facilitate locking the cap 106 in one of the two rotational positions, the platform 403 includes a radially outwardly projecting key 423 (best seen in FIGS. 4, 5 and 8), and the cap 106 defines a slot 800 (best seen in FIGS. 8, 10 and 11). The slot 800 may be somewhat wider than the width 503 (FIG. 5) of the key 423. As best seen in FIG. 8, the key 423 and side slot edges 803 of the cap 106 limit the rotation of the cap 106, thereby locking the cap 106 in an open position. However, by applying sufficient rotational force to the cap 106, one of the side slot edges 803 can be made to deform radially outward and step over the key 423, thereby allowing the cap 106 to be rotated away from the open position. The resilience of the cap 106 determines the amount of force needed to overcome the stopping action of the key. As shown in FIG. 11, the side slot edges 803 may be chamfered, relative to the orientation of the key 423, thereby easing the stepping of the side slot edge 803 over the key 423.

To facilitate locking the cap 106 in the other of the two rotational positions, the cap defines a pocket 1153 (best seen in FIG. 11) sized and configured to accept the key 423. Thus, when the cap 106 is rotated approximately 180 degrees from the open position, the key 423 enters the pocket 1153, and the cap 106 locks in the closed position. Inasmuch as the inside diameter 1138 of the cap 106 is approximately the same as the diameter 500 (FIG. 5) of the platform 403, and the key 423 projects radially outwardly from the platform 403, while the cap 106 is being rotated from the open position to the closed position, the key 423 may rub against the inside wall 1130 of the cap 106 and deflect the wall of the cap 106 radially outward. However, as noted, the cap 106 is resilient. When the cap is rotated to the position where the key 423 is aligned with the pocket 1153, the wall of the cap 106 returns radially inwardly to its natural position, capturing the key 423 within the pocket 1153.

Figure 13:
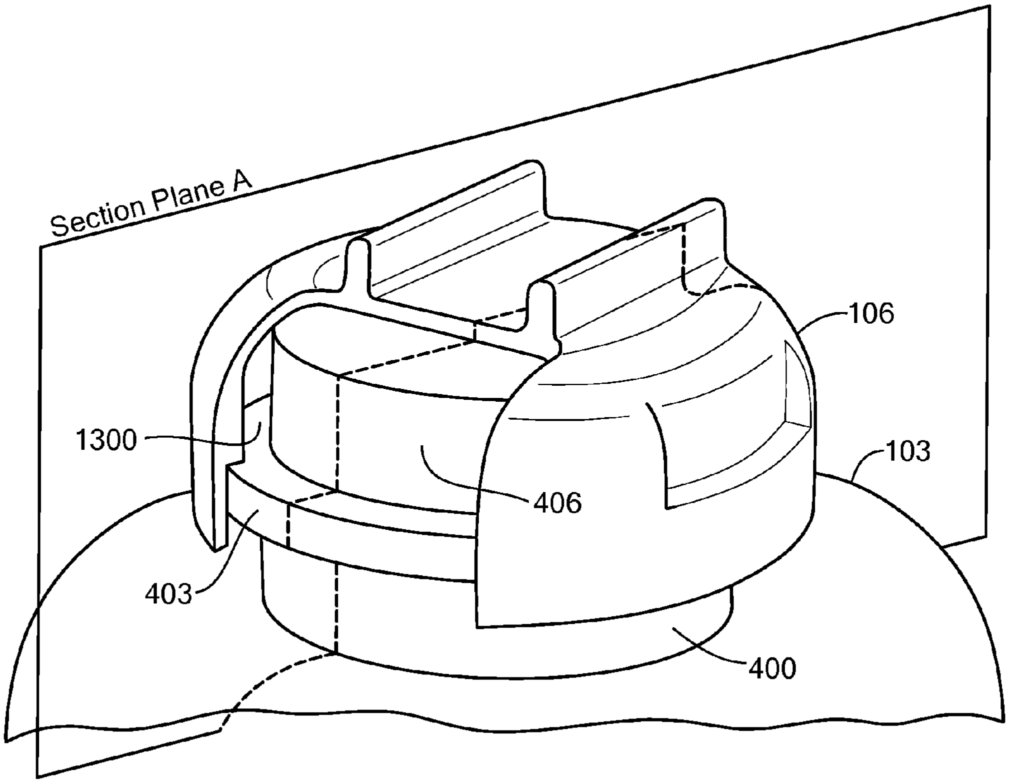
FIG. 13 is a perspective view of the neck portion of the container of FIG. 1, with the cap installed in a second (closed) position, as seen from behind the container.

In addition to providing fluid communication between the nipples 410 and the interior of the bottle 103, the raised curved structure 406 (FIG. 4) is used to close off the slot 800 in the cap 106, when the cap is in the closed position. The raised curved structure 406 is located diametrically opposite the key 423. The curved portion of the raised curved structure 406 subtends an angle about as large as, or larger than, the angle subtended by the slot 800 in the cap 106, and the raised curved structure 406 is tall enough above the platform 403 to effectively block all or most of the slot 800. FIG. 13 is a perspective view of the neck portion of the bottle 103, with the cap 106 in the closed position.

As noted with respect to FIG. 8, the stubs 700 may be tucked in next to each other between the nipples 410 before the cap 106 is closed. Optionally, as shown in FIG. 13, a space 1300 may be left between the raised curved structure 406 and the inside wall of the cap 106. If the stubs 700 are not tucked in as described above, the stubs may be swept around the raised curved structure 404 as the cap is rotated to the closed position (not shown).

By applying sufficient rotational force, the cap 106 can be rotated away from the closed position. However, the force necessary of overcome the resistance of the key 423 being captured by the pocket 1153 is greater than the force necessary to overcome the resistance of the key 423 being captured by the slot 800, because the pocket 1153 is defined by solid material, whereas the slot 800 is open.

As noted with respect to FIG. 2, the tubes 110 may be wrapped longitudinally around the container 100. The key 423 (FIG. 4) should be oriented, relative to the recess 113 in the bottom 300 of the bottle 103, such that when the cap 106 is locked in either position, the vanes 116 are approximately parallel with the recess 113. Preferably, the vanes 116 are approximately parallel to the side slot edges 803 of the cap 106, and the key 423 extends in a radial direction approximately aligned with the recess 113.

Although an embodiment with a key 423 (FIG. 4) that extends radially outward from the platform 403 has been described, other embodiments may include a recess instead. That is, the platform 403 may define one (or two diametrically opposed) recess(es) extending radially inward, and the cap may include one (or two diametrically opposed) complementarily-shaped key(s) extending radially inward.

While the invention is described through the above-described exemplary embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s).

What is claimed is:

1. A container for collecting and storing blood plasma, the container comprising:

a bottle having a neck, the neck having a disc-shaped neck track, the track including a first key;

means for permitting fluid communication into and out of an interior of the bottle; and a cap attachable to the neck and having an internal cap track sized and positioned to cooperate with the neck track and configured to permit the cap to rotate about the neck track, the cap defining a slot sized and positioned to interlock with the first key at a first rotational position of the cap where the means for permitting fluid communication is accessible from outside the cap, the cap further defining a second key sized and positioned to interlock with the first key at a second rotational position of the cap where the means for permitting fluid communication is inaccessible from outside the cap.

2. A container according to claim 1, wherein:

the bottle has a bottom and a major longitudinal axis and defines a recess across a diameter of the bottom of the bottle; and the cap further comprises two spaced-apart vanes extending in directions substantially parallel to the major longitudinal axis of the bottle, such that, at the first rotational position of the cap, the vanes are substantially parallel to the recess in the bottom of the bottle.

3. A container according to claim 1, wherein, at the first rotational position of the cap, the means for permitting fluid communication is accessible from outside the cap via the slot, and at the second rotational position of the cap, the means for permitting fluid communication is inaccessible from outside the cap via the slot.

4. A container according to claim 3, wherein the neck includes a curved structure configured to close off the slot at the second rotational position of the cap.

5. A container according to claim 1, further comprising:

a flexible tube attached at a proximal end thereof to the means for permitting fluid communication and sealed at a distal end thereof and wherein:

the interior of the bottle is sterile.

6. A container according to claim 1, wherein the first key is radially proud of the neck track.

7. A container according to claim 6, wherein:

the first key comprises first, second and third edges in a plane of the neck track, the second edge being parallel to a line tangent to the neck track; and the cap defines the second key as a recess shaped to accept the first key.

8. A container according to claim 7, wherein the first key is rectangular, as viewed in the plane of the neck track.

9. A container according to claim 1, wherein the cap comprises at least one radially inwardly oriented tab projecting from an inside wall of the cap, each of the at least one tab being sized and configured to at least partially prevent a top of another cap from nesting within the cap.

10. A container according to claim 9, wherein the at least one radially inwardly oriented tab at least partially defines the internal cap track.

11. A container according to claim 1, wherein the cap shape is configured to at least partially prevent nesting of the cap within another cap.

12. A container according to claim 1, wherein the cap comprises:

at least one radially inwardly projecting tab on an inside wall of the cap, proximate a circumferential edge of the cap; and at least one radially inwardly projecting track element on an inside wall of the cap, spaced from the circumferential edge of the cap a distance selected to accommodate the disc-shaped neck track between the at least one tab and the at least one track element.

13. A container for collecting and storing blood plasma, the container comprising:

a bottle having a neck, the neck having a disc-shaped neck track, the track including a first key;

at least two ports in fluid communication with an interior of the bottle; and a cap attachable to the neck and having an internal cap track sized and positioned to cooperate with the neck track and configured to permit the cap to rotate about the neck track, the cap defining a slot sized and positioned to interlock with the first key at a first rotational position of the cap where the at least two ports are accessible from outside the cap, the cap further defining a second key sized and positioned to interlock with the first key at a second rotational position of the cap where the at least two ports are inaccessible from outside the cap.

14. A container according to claim 13, wherein:

the bottle has a bottom and a major longitudinal axis and defines a recess across a diameter of the bottom of the bottle; and the cap further comprises two spaced-apart vanes extending in directions substantially parallel to the major longitudinal axis of the bottle, such that, at the first rotational position of the cap, the vanes are substantially parallel to the recess in the bottom of the bottle.

15. A container according to claim 13, wherein, at the first rotational position of the cap, the at least two ports are accessible from outside the cap via the slot, and at the second rotational position of the cap, the at least two ports are inaccessible from outside the cap via the slot.

16. A container according to claim 13, further comprising:

for each of the at least two ports, a flexible tube attached at a proximal end thereof to the port and sealed at a distal end thereof; and wherein:

the interior of the bottle is sterile.

17. A container according to claim 16, wherein the neck includes a curved structure configured to close off the slot at the second rotational position of the cap.

18. A container according to claim 13, wherein the first key is radially proud of the neck track.

19. A container according to claim 18, wherein:

the first key comprises first, second and third edges in a plane of the neck track, the second edge being parallel to a line tangent to the neck track; and the cap defines the second key as a recess shaped to accept the first key.

20. A container according to claim 19, wherein the first key is rectangular, as viewed in the plane of the neck track.

21. A container according to claim 13, wherein the cap comprises at least one radially inwardly oriented tab projecting from an inside wall of the cap, each of the at least one tab being sized and configured to at least partially prevent a top of another cap from nesting within the cap.

22. A container according to claim 21, wherein the at least one radially inwardly oriented tab at least partially defines the internal cap track.

23. A container according to claim 13, wherein the cap shape is configured to at least partially prevent nesting of the cap within another cap.

24. A container according to claim 13, wherein the cap comprises:

at least one radially inwardly projecting tab on an inside wall of the cap, proximate a circumferential edge of the cap; and at least one radially inwardly projecting track element on an inside wall of the cap, spaced from the circumferential edge of the cap a distance selected to accommodate the disc-shaped neck track between the at least one tab and the at least one track element.

* * * * *